United States Patent
Zelvin et al.

(10) Patent No.: US 7,338,167 B2
(45) Date of Patent: Mar. 4, 2008

(54) RETINAL IMAGING SYSTEM

(75) Inventors: Joseph Zelvin, Larchmont, NY (US); Sven-Erik Bursell, Newton, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 123 days.

(21) Appl. No.: 10/732,822

(22) Filed: Dec. 10, 2003

(65) Prior Publication Data
US 2005/0134796 A1 Jun. 23, 2005

(51) Int. Cl.
*A61B 3/14* (2006.01)
(52) U.S. Cl. .................. 351/206; 351/207; 351/221
(58) Field of Classification Search .............. 351/206, 351/207, 214, 221, 210, 246
See application file for complete search history.

(56) References Cited

U.S. PATENT DOCUMENTS

| | | | |
|---|---|---|---|
| 3,851,154 A | 11/1974 | Beecham | |
| 3,851,954 A | 12/1974 | Kato et al. | |
| 3,925,793 A | 12/1975 | Matsumura et al. | |
| 3,984,157 A * | 10/1976 | LeVantine | 351/213 |
| 4,023,189 A | 5/1977 | Govignon | |
| 4,102,563 A | 7/1978 | Matsumura et al. | |
| 4,146,310 A | 3/1979 | Kohayakawa et al. | |
| 4,149,787 A | 4/1979 | Kobayashi et al. | |
| 4,184,752 A | 1/1980 | Richards et al. | |
| 4,196,979 A | 4/1980 | Kohayakawa et al. | |
| 4,238,142 A | 12/1980 | Richards et al. | |
| 4,248,505 A | 2/1981 | Muchel et al. | |
| 4,249,802 A | 2/1981 | Muchel et al. | |
| 4,251,139 A | 2/1981 | Matsumura et al. | |
| 4,253,743 A | 3/1981 | Matsumura et al. | |
| 4,257,687 A | 3/1981 | Kohayakawa | |
| 4,266,862 A | 5/1981 | Trötscher et al. | |
| 4,331,392 A | 5/1982 | Sato | |
| 4,422,736 A | 12/1983 | Nunokawa et al. | |
| 4,453,808 A * | 6/1984 | Takahashi et al. | 351/208 |
| 4,511,227 A | 4/1985 | Nunokawa et al. | |
| 4,657,357 A * | 4/1987 | Nishimura et al. | 359/377 |
| 4,715,703 A | 12/1987 | Cornsweet et al. | |
| 4,732,466 A | 3/1988 | Humphrey | |
| 4,761,066 A | 8/1988 | Carter | |
| 4,786,161 A | 11/1988 | Müller et al. | |
| 4,799,783 A | 1/1989 | Takahashi et al. | |

(Continued)

FOREIGN PATENT DOCUMENTS

CA 1019178 10/1977

(Continued)

OTHER PUBLICATIONS

Dialog Search Results (236 pages).

(Continued)

*Primary Examiner*—Huy Mai
(74) *Attorney, Agent, or Firm*—Fish & Richardson P.C.

(57) ABSTRACT

A retinal imaging system includes a light source and optics which receive light from the light source and which transmit the light to produce a beam that is substantially convergent. The beam penetrates a lens of an eye and diverges following penetration of the lens to illuminate an area of a retina of the eye. An imaging device receives a reflection of light from the retina.

47 Claims, 12 Drawing Sheets

U.S. PATENT DOCUMENTS

| | | |
|---|---|---|
| 4,810,083 A | 3/1989 | Okada et al. |
| 4,881,807 A | 11/1989 | Luce et al. |
| 4,989,023 A | 1/1991 | Sakurai et al. |
| 4,991,584 A | 2/1991 | Kobayashi et al. |
| 4,998,818 A | 3/1991 | Kugler et al. |
| 5,018,851 A | 5/1991 | Matsumura |
| 5,037,194 A | 8/1991 | Kohayakawa et al. |
| 5,042,939 A | 8/1991 | Zayek |
| 5,071,246 A | 12/1991 | Blaha et al. |
| 5,120,122 A | 6/1992 | McAdams |
| 5,233,517 A | 8/1993 | Jindra |
| 5,255,026 A | 10/1993 | Arai et al. |
| 5,302,988 A | 4/1994 | Nanjo |
| 5,315,329 A | 5/1994 | McAdams |
| 5,333,018 A | 7/1994 | Heine et al. |
| 5,471,237 A | 11/1995 | Ship |
| 5,506,634 A * | 4/1996 | Wei et al. ............... 351/221 |
| 5,532,769 A | 7/1996 | Miwa et al. |
| 5,557,321 A | 9/1996 | Kohaykawa et al. |
| 5,572,266 A | 11/1996 | Ohtsuka et al. |
| 5,612,816 A | 3/1997 | Strahle et al. |
| 5,627,613 A * | 5/1997 | Kaneko ............... 351/221 |
| 5,633,695 A | 5/1997 | Feke et al. |
| 5,668,621 A | 9/1997 | Nanjo |
| 5,713,047 A | 1/1998 | Kohayakawa |
| 5,742,374 A | 4/1998 | Nanjo et al. |
| 5,751,396 A | 5/1998 | Masuda et al. |
| 5,847,805 A | 12/1998 | Kohayakawa et al. |
| 5,867,249 A | 2/1999 | Ichiki et al. |
| 5,940,425 A | 8/1999 | Lasser et al. |
| 5,943,116 A | 8/1999 | Zeimer |
| 5,993,001 A | 11/1999 | Bursell et al. |
| 6,065,837 A | 5/2000 | Goldfain et al. |
| 6,139,151 A * | 10/2000 | Ueno et al. ............... 351/220 |
| 6,296,358 B1 | 10/2001 | Cornsweet et al. |
| 6,456,787 B1 | 9/2002 | Matsumoto et al. |
| 6,636,696 B2 | 10/2003 | Saito |
| 2003/0208125 A1* | 11/2003 | Watkins ............... 600/473 |
| 2004/0085627 A1* | 5/2004 | Okamura et al. ............ 359/385 |

FOREIGN PATENT DOCUMENTS

| | | |
|---|---|---|
| CA | 1029584 | 4/1978 |
| CA | 2054441 | 7/1996 |
| DE | 27 25 990 | 12/1977 |
| EP | 0 428 450 | 5/1990 |
| GB | 2203260 | 10/1988 |
| JP | 9000496 | 1/1977 |
| JP | 9192130 | 7/1977 |
| WO | WO 200030527 | 6/2000 |

OTHER PUBLICATIONS

Notification of Transmittal of the International Search Report and the Written Opinion of the International Searching Authority, or the Declaration, 1 page (Oct. 28, 2005).

Notification of Transmittal of the International Search Report, 4 pages (Oct. 28, 2005).

Written Opinion of the International Searching Authority, 7 pages (Oct. 28, 2005).

* cited by examiner

RETINAL IMAGING SYSTEM

TECHNICAL FIELD

This patent application relates generally to a retinal imaging system and, more particularly, to a nonmydriatic retinal imaging system that substantially segregates illumination light from imaging light.

BACKGROUND

FIG. 1 shows a side-view of an eye 10. Eye 10 includes a cornea 11, an iris 12, a pupil 14, a lens 15, and a retina 16. Light enters the eye through pupil 14, is focused and inverted by cornea 11 and lens 15, and is projected onto retina 16 at the back of the eye. Iris 12 acts as a shutter that can be opened or closed to regulate the amount of light entering the eye via pupil 14.

Retina 16 is a seven-layered structure that converts received light into a neural signal. This conversion process is known in the art as "signal transduction". The actual photoreceptors on the retina are rods and cones, but the cells that transmit the resulting neural signal to the brain are ganglion cells. The axons of these ganglion cells make up the optic nerve 17.

Retinal imaging systems operate by directing light into a patient's eye to illuminate a portion of the retina. A camera captures an image of the illuminated portion of the retina via light reflected off of the retina. Obtaining a clear retinal image has proven difficult in the past due, at least in part, to mingling of light used for illumination with light used for imaging and, in part, due to the reflections off of the cornea. For example, traditional retinal imaging systems use inner and outer paths (e.g., concentric paths) for imaging and illumination, respectively. In these systems, light from the illumination path often mingled with light for imaging, resulting in poor quality images.

SUMMARY

In general, in one aspect, the invention is directed to a retinal imaging system that includes a light source and optics which receive light from the light source and which transmit the light to produce a beam that is substantially convergent. The beam penetrates a lens of an eye and diverges following penetration of the lens to illuminate an area of a retina of the eye. An imaging device receives a reflection of light from the retina. This aspect may include one or more of the following features.

The optics may include a beam splitting device that allows transmission of at least part of the light away from the eye. The system may include a darkened region for absorbing the part of the light transmitted away from the eye, and/or a surface containing an aperture that is positioned in front of the eye for blocking at least some Purkinje reflections and corneal reflections from the eye. The surface may be covered, at least in part, with a non-reflective material. The system may include surfaces that form an aperture located between the light source and the optics. The aperture may limit an angle of the light to reach the optics. The system may include a series of surfaces that form a series of apertures located between the light source and the optics. The series of apertures may limit an angle of the light to reach the optics.

The system may include rilling located along a path the light takes between the light source and the optics, and a stereo filter may be located on an optical path between the eye and the imaging device. The stereo filter may include an area for transmitting a first portion of imaging rays from the eye and an area for blocking a second portion of the imaging rays. The first portion of imaging rays may include rays obtained at a first angle from a point on the retina, and the second portion of imaging rays may include rays obtained at a second angle from the point on the retina. The system may include at least one housing that holds the light source, the optics, and the imaging device, and a mechanism for positioning the at least one housing relative to the eye. The housing may be movable to change the area of the retina that is illuminated. The light source may include light emitting diodes having different colors, and/or optical fiber arranged to receive light from at least one of the light emitting diodes.

In general, in another aspect, the invention is directed to an ophthalmoscope that includes optics which direct light into a predetermined portion of an eye that is not used for imaging. The optics shape the light so that the light is substantially convergent as the light goes through a lens of the eye and so that the light diverges following penetration of the lens to illuminate an area of a retina of the eye. An imaging device captures images of the retina. This aspect may include one or more of the following features.

The optics may include a beam splitting device that transmits at least part of the light away from the eye. The ophthalmoscope may include a darkened region for absorbing the part of the light transmitted away from the eye, and surface containing an aperture that is positioned in front of the eye for blocking at least some Purkinje reflections from the eye. The surface may be covered, at least in part, with a non-reflective material. The ophthalmoscope may include a light source that provides the light to the optics and surfaces that form an aperture located between the light source and the optics. The aperture may limit an angle of the light to reach the optics. A series of surfaces may form a series of apertures located between the optics and a source of the light. The series of apertures may limit an angle of the light to reach the optics.

The ophthalmoscope may include rilling located along a path the light takes between a source of the light and the optics. A stereo filter may be located on an optical path between the eye and the imaging device. The stereo filter may include an area for transmitting a first portion of imaging rays from the eye and an area for blocking a second portion of the imaging rays. The first portion of imaging rays may include rays obtained at a first angle from a point on the retina, and the second portion of imaging rays may include rays obtained at a second angle from the point on the retina. The ophthalmoscope may include a light source that provides the light to the optics, at least one housing that holds the light source, the optics, and the imaging device, and a mechanism for positioning the at least one housing relative to the eye. The housing may be movable to change the area of the retina that is illuminated. The ophthalmoscope may include a light source comprised of light emitting diodes having different colors, and/or optical fiber arranged to receive light from at least one of the light emitting diodes and to deliver the light to the optics.

In general, in another aspect, the invention is directed to a retinal imaging apparatus, which includes means for producing convergent light and for directing the convergent light to a lens of an eye so that the convergent light diverges following penetration of the lens and illuminates a retina of the eye, means for capturing an image of the retina, and means for selectively blocking light reflected from the retina from the means for capturing. This aspect may also include any features described herein.

In general, in another aspect, the invention is directed to a retinal imaging system that includes an illumination path which receives light, and which causes the light to penetrate a pupil of an eye at a spot on the pupil. The light exits the lens to illuminate an area of a retina of the eye. The system also includes an imaging path which receives reflected light from the area of the retina and which transmits the reflected light to an imaging device. The imaging path contains surfaces that define apertures to reduce Purkinje reflections and to reduce reflections from an iris of the eye. The imaging path contains a stereo filter having one area for passing a first portion of the reflected light and another area for blocking a second portion of the reflected light. This aspect may also include one or more of the following features.

The system may include a base on which the illumination path and the imaging path are mounted. The base may provide five degrees of freedom of motion for the retinal imaging system. The base may be a slit lamp base. The illumination path may include a beam splitting device that transmits at least part of the light away from the eye. The system may include a darkened region for absorbing the part of the light transmitted away from the eye. The illumination path may include a series of surfaces that form a series of apertures located along the illumination path. The series of apertures may limit an angle of the light to reach the eye.

The system may include rilling located along the illumination path. The first portion of reflected light may include light reflected at a first angle from a point on the retina, and the second portion of reflected light may include light reflected at a second angle from the point on the retina. The system may include a light source comprised of different color diodes which provide the light to the illumination path, and a beam splitter that transmits at least part of the light from the illumination path away from the eye.

In general, in another aspect, the invention is directed to a method that includes generating convergent light via an illumination path of a retinal imaging system, directing the convergent light through an illumination portion of an eye, where the illumination portion of the eye is segregated from an imaging portion of the eye, receiving reflected light via the imaging portion of the eye, passing the reflected light through an imaging path to an image capturing device, and producing an image based on the reflected light. The method may include one or more of the following features.

The method may include selectively blocking a portion of the reflected light to produce a stereo image of the eye. Selectively blocking the portion of the light may include transmitting a first portion of the reflected light and blocking a second portion of the reflected light. The first portion may include rays obtained at a first angle from a point on the retina, and the second portion may include rays obtained at a second angle from the point on the retina. The method may include blocking at least some Purkinje reflections from reaching the imaging path. The convergent light may be generated via one or more of optics, rilling, apertures, colored diodes, and/or white diodes.

The foregoing aspects may be used to illuminate and image the retina of a subject. The subject may be a human subject over the age of 60 years old. The pupil of the eye being imaged in the subject may be dilated to less than or equal to 2.5 mm. The subject may have one more of the following: diabetes including diabetic retinopathy and/or macular edema, glaucoma, optic cup/disc asymmetry, macular drusen, retinal pigment epithelial changes, age-related macular degeneration, hypertensive retinopathy, retinal emboli, retinal vein occlusion, preretinal hemorrhage, vitreous hemorrhage, traction retinal detachment, choroidal nevus, choroidal lesions, epiretinal membrane, asteroid hyalosis, chorioretinal scar/atrophy, optic disc hemorrhage, and a macular hole.

In general, in another aspect, the invention is directed to a method of imaging a retina of an eye of a subject. The method includes generating convergent light via an illumination path of a retinal imaging system, directing the convergent light through an illumination portion of the eye, where the illumination portion of the eye is segregated from an imaging portion of the eye, receiving reflected light via the imaging portion of the eye, passing the reflected light through an imaging path to an image capturing device, and producing an image of the retina based on the reflected light. The method may be performed on a subject suspected of having a condition. The condition may relate to one or more of the following: diabetes including diabetic retinopathy and/or macular edema, glaucoma, optic cup/disc asymmetry, macular drusen, retinal pigment epithelial changes, age-related macular degeneration, hypertensive retinopathy, retinal emboli, retinal vein occlusion, preretinal hemorrhage, vitreous hemorrhage, traction retinal detachment, choroidal nevus, choroidal lesions, epiretinal membrane, asteroid hyalosis, chorioretinal scar/atrophy, optic disc hemorrhage, and a macular hole.

In general, in another aspect, the invention is directed to a method of diagnosing a condition using a retinal imaging system comprised of an illumination path which receives light, and which causes the light to penetrate a pupil of an eye at a spot on the pupil, and an imaging path which receives reflected light from a retina of the eye and which transmits the reflected light to an imaging device. The method includes rotating at least part of the illumination path relative to the eye, and generating images via the imaging device that include shadows indicative of details of the eye. This aspect may include one or more of the following features.

The images may include video. The condition may relate to one or more of the following: diabetes including diabetic retinopathy and/or macular edema assessment, glaucoma, optic cup/disc asymmetry, macular drusen, retinal pigment epithelial changes, age-related macular degeneration, hypertensive retinopathy, retinal emboli, retinal vein occlusion, preretinal hemorrhage, vitreous hemorrhage, traction retinal detachment, choroidal nevus, choroidal lesions, epiretinal membrane, asteroid hyalosis, chorioretinal scar/atrophy, optic disc hemorrhage, and a macular hole.

These and other advantages of the invention will become apparent from the following description, including the drawings and claims.

DESCRIPTION OF THE DRAWINGS

Like reference numerals in different figures indicate like elements.

DESCRIPTION

Figure 1:
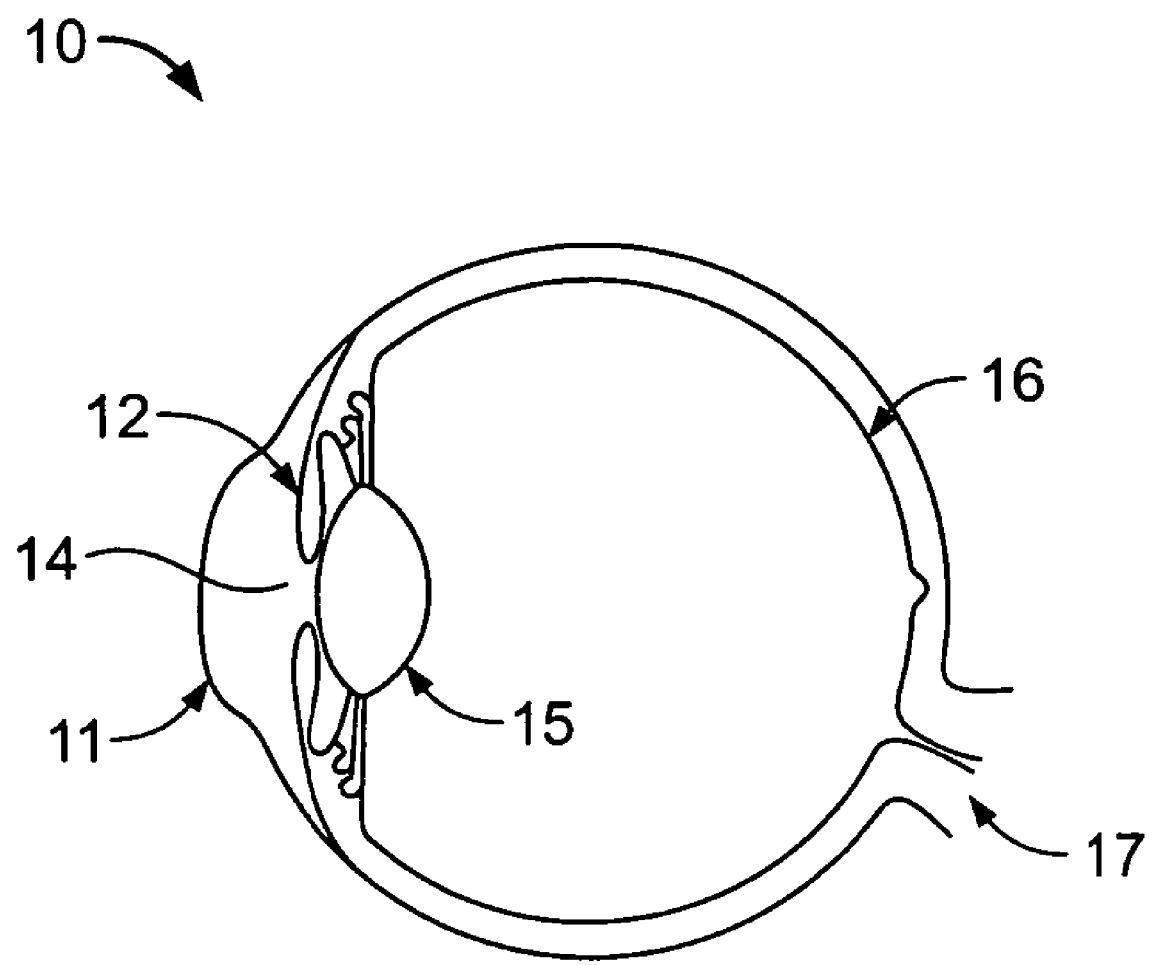
FIG. 1 is diagram showing a cross-sectional side view of a human eye.
Figure 2:
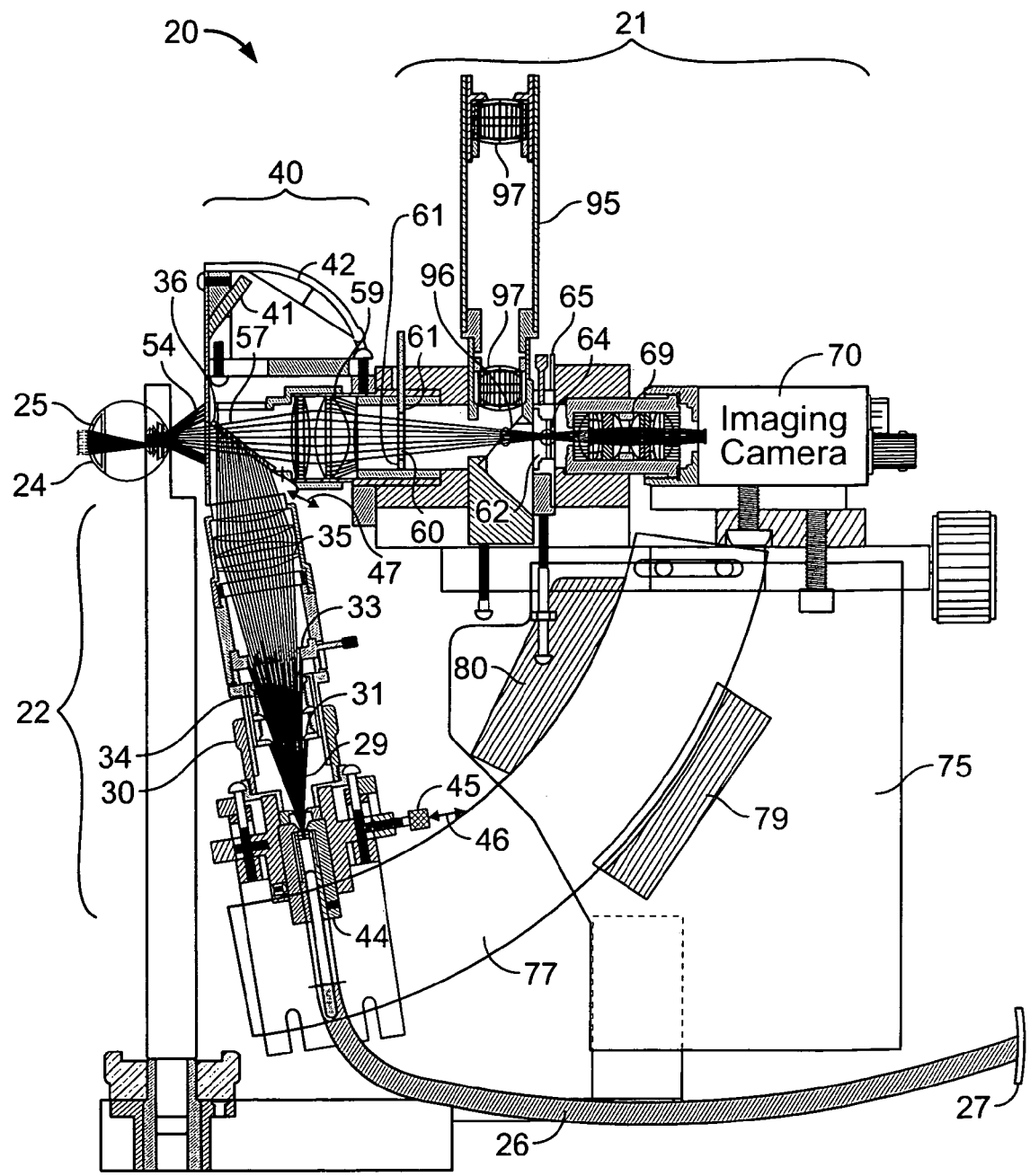
FIG. 2 is a side view of a retinal imaging system.
Figure 3:
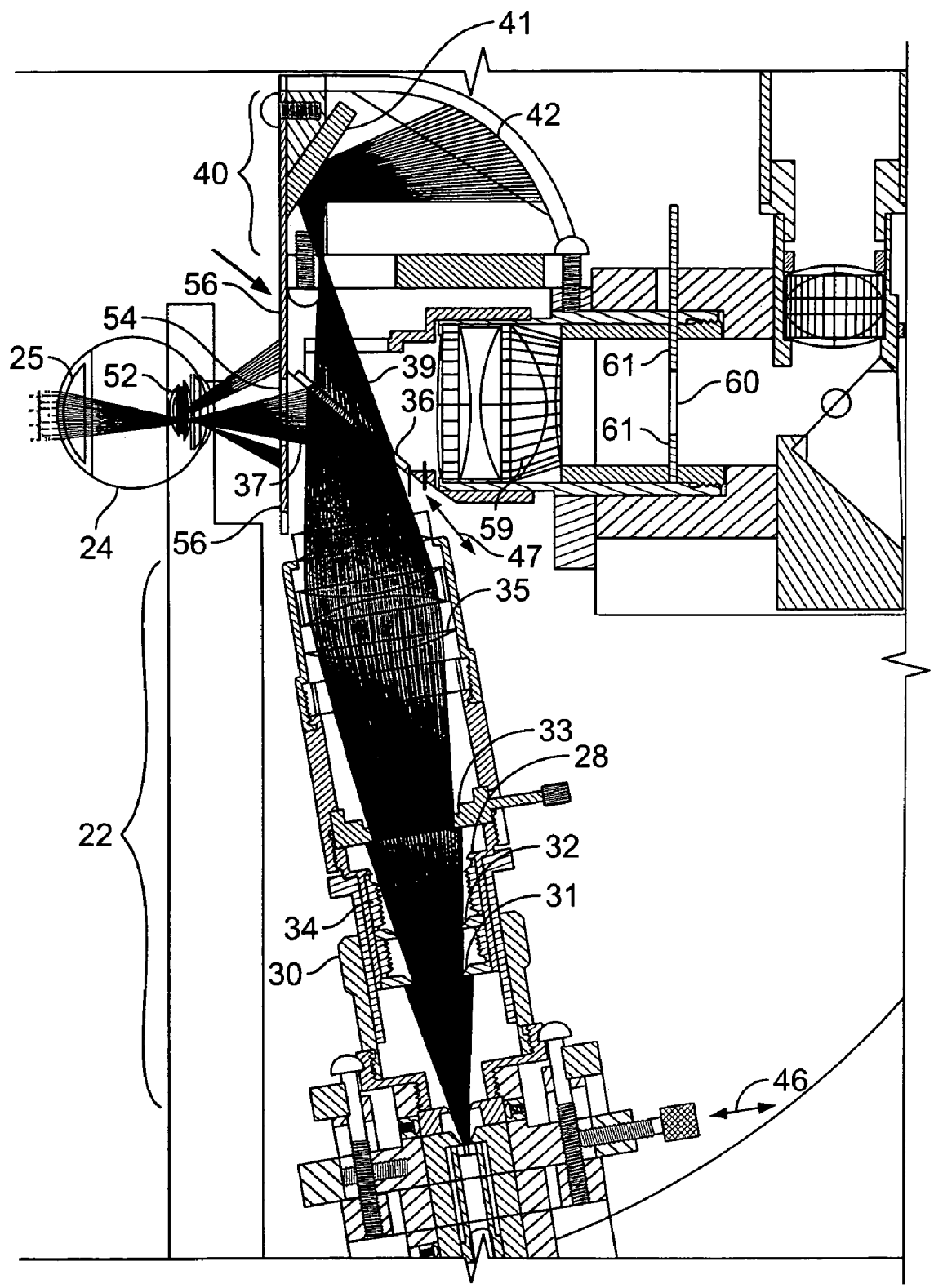
FIG. 3 is a close-up view of an illumination path in the retinal imaging system of FIG. 2.

FIGS. 2 and 3 show retinal imaging system 20. Retinal imaging system 20 includes an imaging path 21 and an assembly 22 comprising an illumination path. Assembly 22 includes structures to direct light into a patient's eye 24 (in particular, onto retina 25), and imaging path 21 includes structures to direct light reflected from the retina back to an image capturing device, such as a film-based camera or a charge coupled device (CCD) or any other light sensitive video imaging sensor. The camera may be monochromatic. Color images can be obtained by varying colors of illumination sources, as described in more detail below.

In this embodiment, light from illumination path enters the eye at an angle relative to imaging path 21. This ensures that illumination light entering the eye is not reflected directly into imaging path 21 and thereby adversely affect the quality of resulting images.

Assembly 22 receives light via a fiber optic cable 26 (other embodiments may receive light via other means). Fiber optic cable 26 is comprised of one or more optical fibers that are capable of transmitting light from a light source 27 to assembly 22. In this embodiment, the fiber optic cable is 1/16 inch in diameter; however, other sizes of fiber optic cable may be used.

Light source 27 is a collection of light-emitting diodes (LEDs) arranged at the end of fiber optic cable 26. Red, green and blue LEDs may be used. These LEDs may be selectively illuminated to provide light to assembly 22 that is red, green, blue, or other colors. The LEDs may be illuminated sequentially. The resulting images may be combined using software to produce an image that corresponds to a "white light" image (or any other type of "color balanced" image).

The brightness of the LEDs may vary depending upon a number of factors. For example, LEDs with ratings of 20 ma to 350 ma, or even up to 1000 ma (or more) may be used. The brightness of these diodes is proportional to their current, so there is a gain of roughly 50 times the light output, which is at least five "f-stops". There is essentially no recovery time required for diodes. This makes live video possible via retinal imaging system 20. Furthermore, diodes can last for 100,000 hours, thus obviating the need for frequent bulb replacement.

Heretofore, retinal imaging systems generally used electronic flash (Xenon) or scanning lasers. Their flash units are essentially white light, so they are able to take real color pictures via very high-cost digital cameras or three-chip analog or digital video cameras. Such color cameras "create" color images by use of a Bayer-type filter over the camera chip, which reduces the light reaching the chip and reduces the real spatial resolution of the camera to 1/4 of the pixel count. The use of a Bayer-type filter involves interpolation in order to derive the color of each pixel. All sorts of color artifacts result from this interpolation process, especially interference patterns when dealing with high pixel counts. Three-chip analog cameras use a prism to separate red, green and blue components by putting a primary color filter in front of each chip. This method is also costly.

The use of a monochromatic camera enables the retinal imaging system to take advantage of the much greater sensitivity of the camera chip. This means that less light needs to be provided to the patient. A 640×480 monochromatic camera produces the same spatial color resolution as a 1280×1024 color camera (because of the color camera's use of a Bayer filter). Plus, the monochromatic camera is less costly, more sensitive than the above options, and produces substantially the same resolution.

The "high power" diodes used in retinal imaging system 20 have made solid state lighting achievable. In this embodiment, the diodes are approximately 5 mm in diameter, and 10% to 20% of the useful flux emanates from the center 1/16 of the diode (which corresponds substantially to the diameter of the optical fiber). Much of the light produced by the diode may not be used, as the diode produces a very wide beam of light and retinal imaging system 20 only uses roughly the center 15° of that beam. However, the more light that is obtained from the source (i.e., the diodes), the shorter the exposure needed to obtain retinal imaging. Shorter exposures create sharper pictures and help to reduce after-images for the patient, thus making the exam more comfortable.

To create a color image, red, green and blue (RGB) frames may be combined in software and color-balanced to a preset standard. Software may be run in a computer that connects to the image capturing device (e.g., camera). To account for motion between frames, the software finds features in each frame that allow proper alignment. This will occur in both left and right frames. Software may also enable retinal imaging system 20 to take many image sequences during an exam. The software may then automatically pick the best frame of each sequence to use as an image.

Taking separate red, green, and blue images permits color balancing "on-the-fly", meaning that retinal imaging system captures each color frame as a well exposed image, rather than adjusting the exposure in post-processing. It is noted that retinal imaging system 20 is not limited to red, green, and blue imaging. Special exams can be performed without using color filters or using different filters, e.g., red-free, blue only, or even infra-red by using an appropriate diode.

Light from brighter LEDs may need to be controlled before being directed into the patient's eye. Structures to control the light entering the eye are described below. The structures noted below are used to "clean up" the stray light, not necessarily to reduce the light (although some reduction in the amount of light entering the eye may occur). Shortening exposure time or electronically dimming the diodes can more effectively reduce the light impinging on a retina. These methods also may be used to balance different colors relative to each other.

Light 29 exiting fiber optic cable 26 enters assembly 22. Assembly 22 contains a series of apertures 28 and 31 to 33 (and may contain one or more others at the termination of the fiber) formed by surfaces referred to herein as "baffles". The baffles may be circular apertures that limit the angle of light able to pass through the baffles within assembly 22. Surfaces of the apertures may be coated with non-reflective material to reduce reflections within housing 30. Apertures 28 and 31 to 33 (and others) may be the same size (shown) or may have different sizes.

The interior surface of assembly 22 may contain rilling 34. Rilling 34 is a serrated (or, more generally, uneven) surface. Such a surface serves to diffuse stray light within housing 30, rather than reflecting that light uniformly. Rilling 34 may be coated with a non-reflective material so as to diffuse the stray light even further and thereby provide further control over the light.

Figure 4:
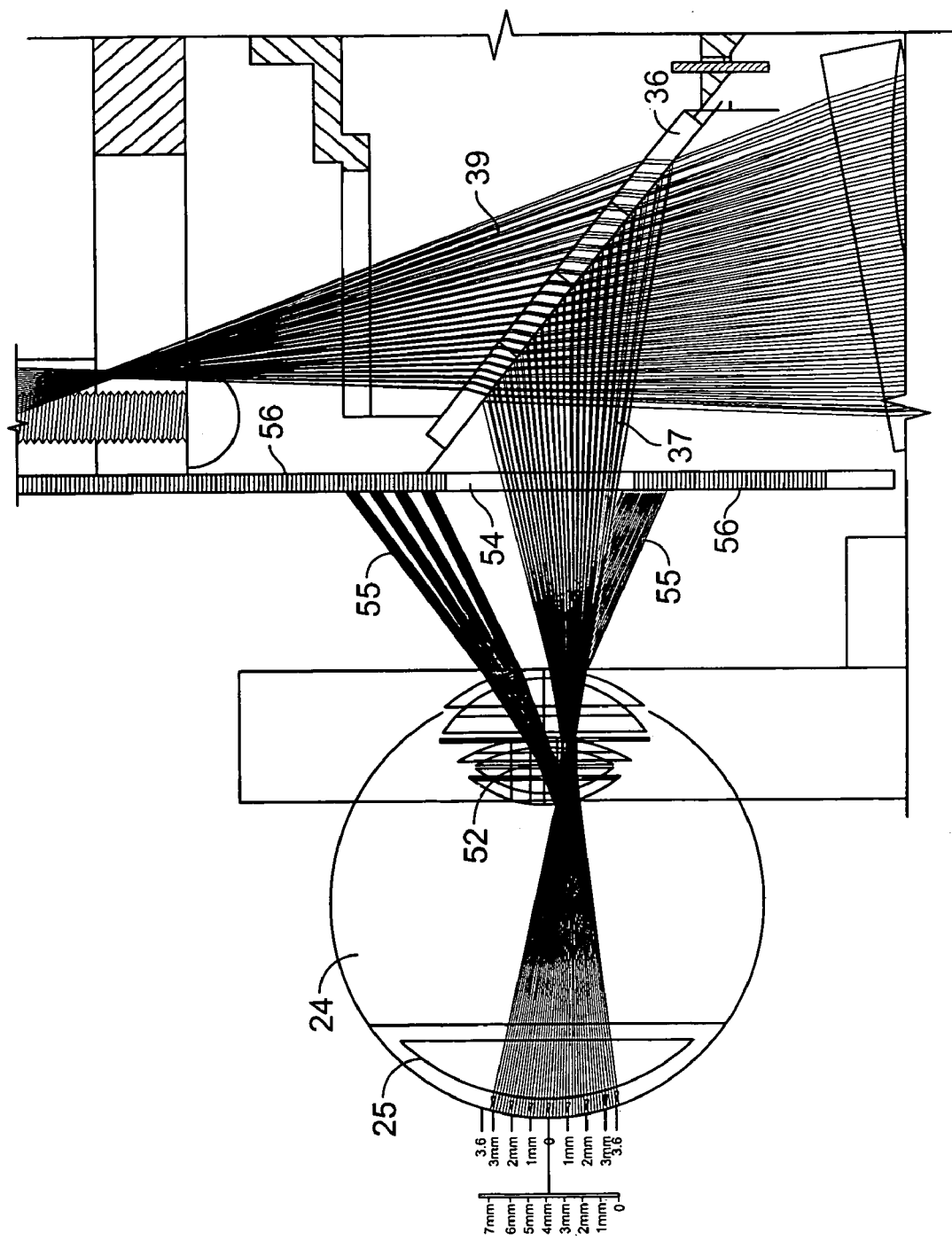
FIG. 4 is a close-up view of light entering an eye from the retinal imaging system of FIG. 2.

Optics 35 direct light from the illumination path, namely assembly 22, to eye 24. Optics 35 (including the optics in assembly 22) includes one or more lenses, which may be convex and/or concave. These lenses direct light from assembly 22 to beam splitter 36. Beam splitter 36 may be a plate, membrane, prism, or other optic device known to those skilled in the art that reflects a preferred fraction of the light as a mirror might, and that allows the remaining fraction of the light to pass. As shown in FIGS. 3 and 4, beam splitter 36, directs some light 37 from illumination optical path into eye 24. The amount of light that is so directed is dictated by the amount of light needed for imaging. The shape of beam splitter 36 and, perhaps more importantly, the materials from which it is made, have an effect on the amount of light that is directed into eye 24.

Light 39 that is not directed into eye 24 by beam splitter 36 is directed to beam absorption assembly 40. Beam absorption assembly 40 includes a mirror 41. Mirror 41 directs received light to a light absorbing surface 42. Light absorbing surface 42 may be any type of surface that contains a non-reflective (e.g., dark and/or rough, etc.) coating.

Fiber optic cable 26 is held in place via casing 44. Adjuster 45 may be used to move casing 44. Specifically, adjuster 45 is threaded, as shown, so that it can be screwed, thereby moving casing 44 (and thus fiber optic cable 26) laterally (in a direction of arrow 46).

Lateral motion of fiber optic cable 26 causes light 29 emitted therefrom to move longitudinally along beam splitter 36 in a direction of arrow 47. This motion on beam splitter 36 translates to vertical motion relative to the patient's eye. Thus, the lateral motion of fiber optic cable 26 produced by adjuster 45 acts to position light vertically on the patient's eye 24. This motion constitutes a "fine" vertical adjustment, as opposed to more coarse vertical adjustments of retinal imaging system 20.

Illumination light 37 is directed into eye 24 at a specific angle and position relative to imaging path 21 that optimizes the separation of illumination and imaging rays, illuminates the portion of interest of the retina, and does not allow substantial illumination rays to reach the imaging device (camera, CCD, video camera, or human eye that is viewing the retina). This is enhanced by various baffles in the imaging path that block unwanted, non-imaging rays. Directing light into the eye at an angle of 0° (on-axis only) could cause direct reflections, resulting in poor image quality.

Light 37 converges as it approaches, and enters, the patient's eye, thereby creating a "point source" of convergent light. At the point of entry, a cross-section of the light (i.e., the resulting "spot") will be substantially circular to substantially oval in shape. Among other things, the "point source" of light reduces the chances that aberrant opaque ocular optical structures, such as cataracts will be imaged.

Figure 5:
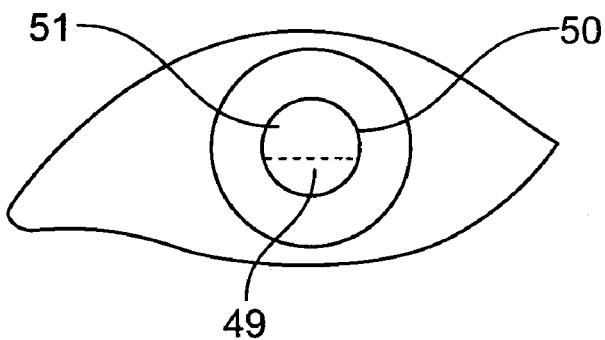
FIG. 5 is a front view of the eye of FIG. 4.
Figure 6:
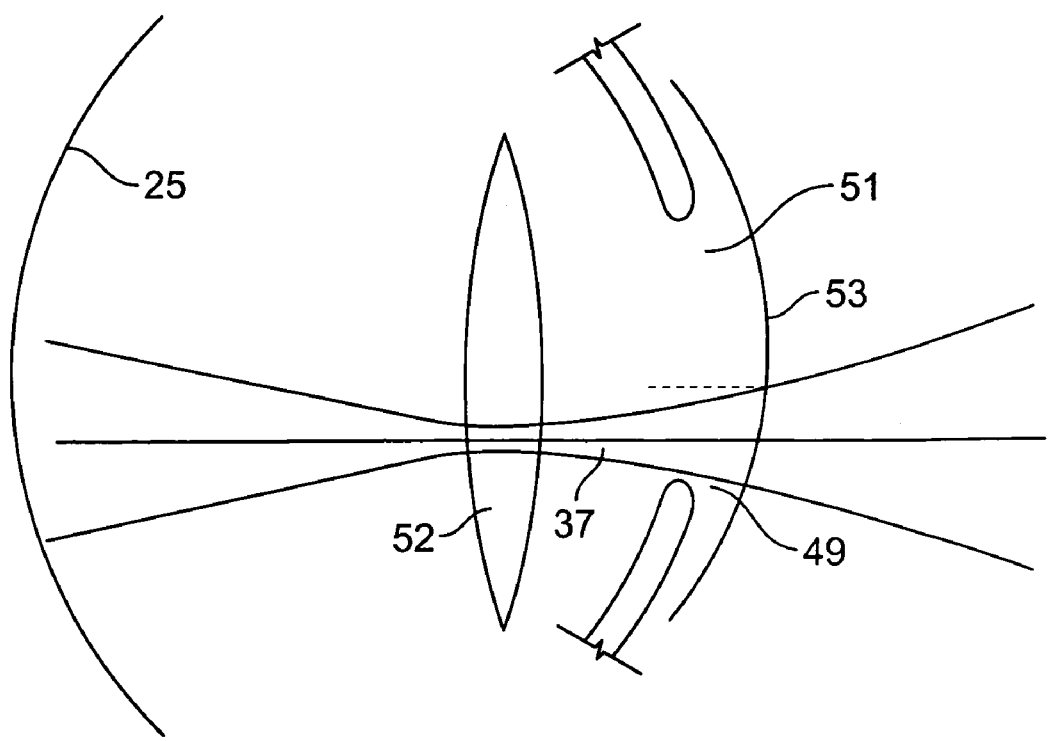
FIG. 6 is a cross-sectional side view of the lens of the eye of FIG. 4 and of light entering the lens.

Referring to FIG. 5 and 6, light 37 is directed into a designated illumination portion 49 of eye 24's pupil 50. The remainder 51 of the pupil, used as the imaging portion, is used to capture images of the eye's retina 25. That is, reflections of light from the retina are captured via the imaging portion 51. The sizes of illumination portion 49 and imaging portion 51 may vary based on the size of the patient's pupil. In one embodiment, for a 3.5 mm pupil, the upper 2.5 mm constitutes the imaging portion and the lower 1 mm constitutes the illumination portion. By segregating the imaging light from the illumination light, relatively clear retinal images may be obtained.

Figure 11:
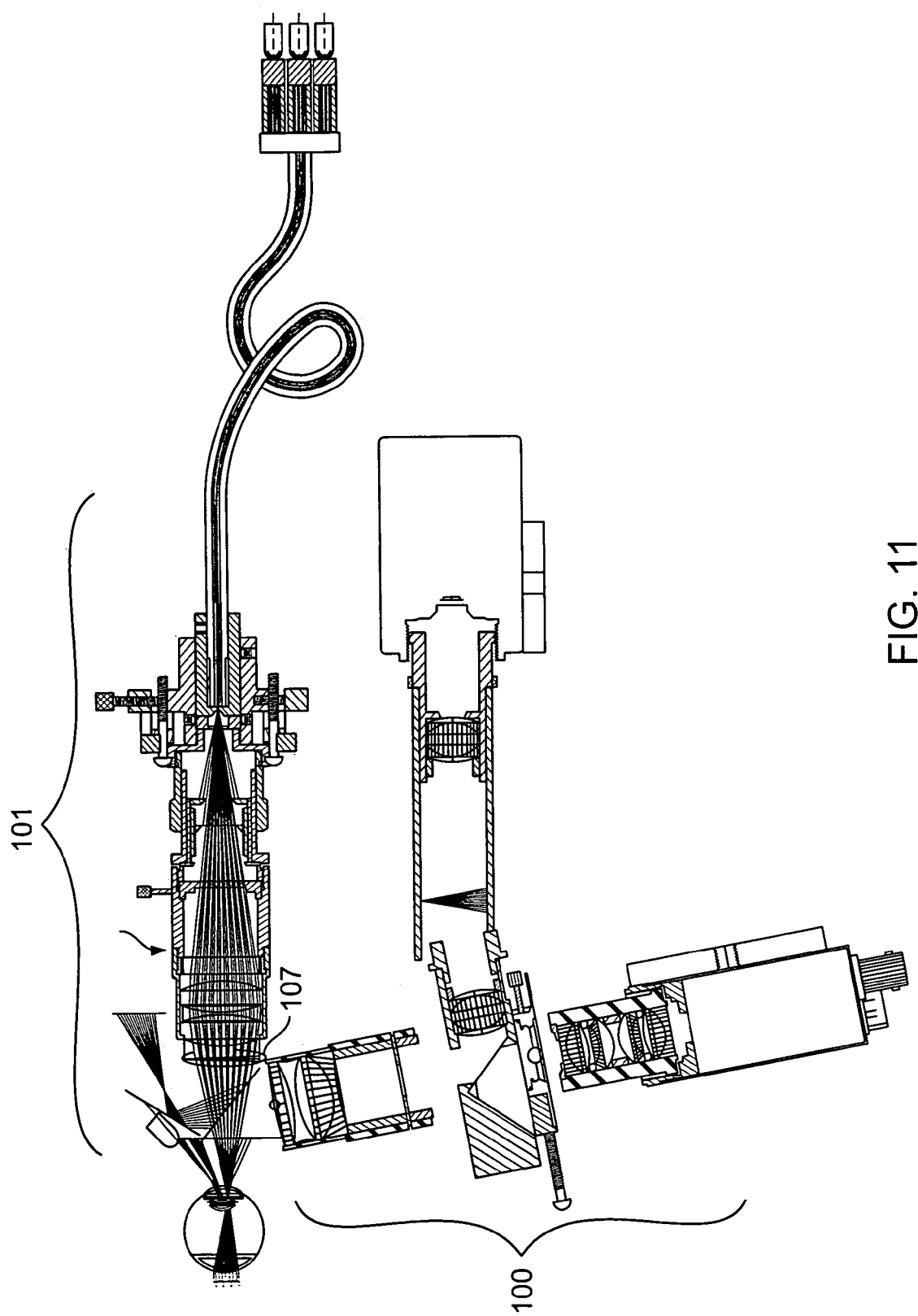
FIG. 11 is a side view of a second embodiment of the retinal imaging system.
Figure 12:
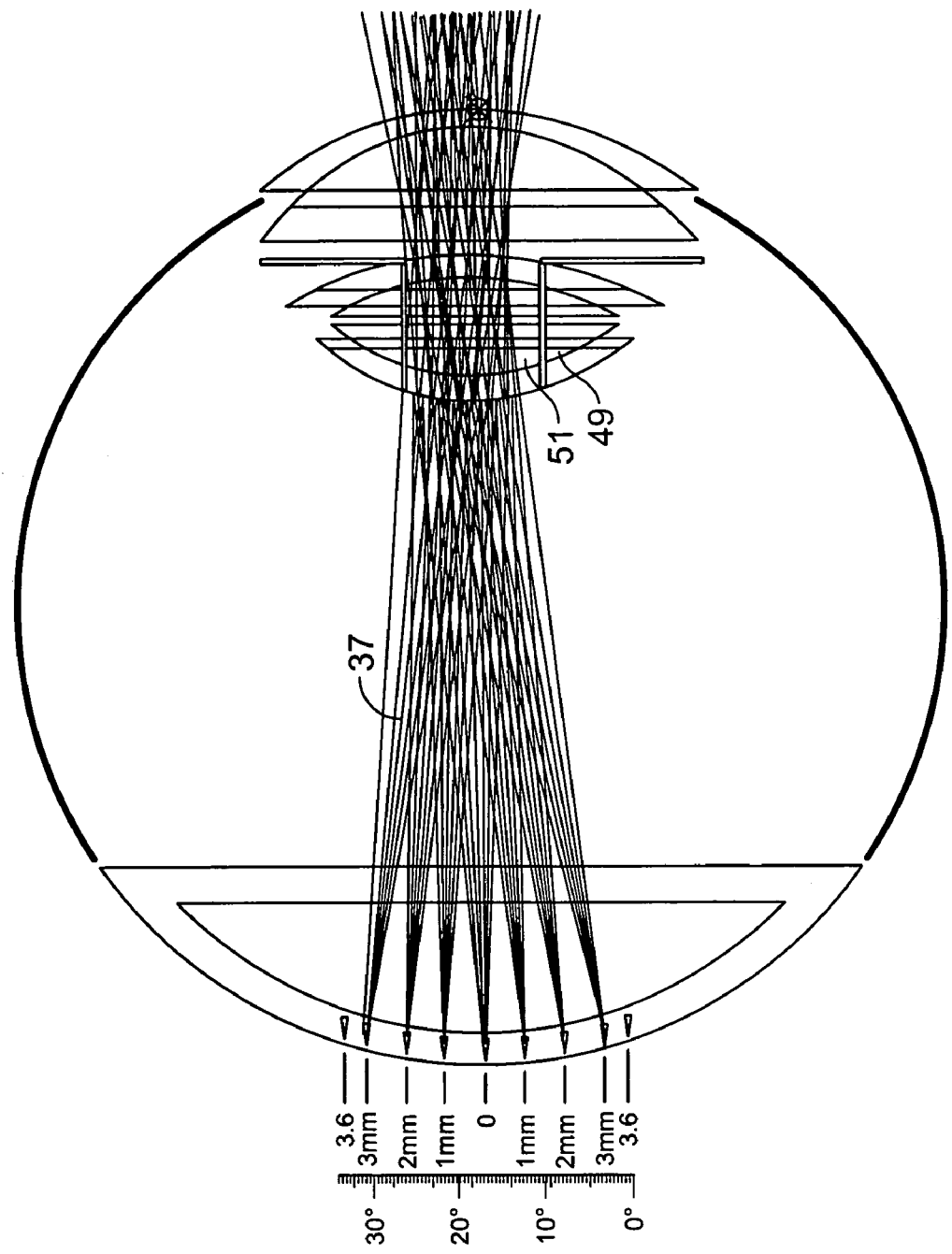
FIG. 12 is a side view showing imaging rays reflecting from a retina.

Light 37 continues to converge until it reaches the lens of the eye 52 or a point in front of the lens. This is shown in FIG. 6. Cornea 53 refracts the light as it enters the eye. At or in front of lens 52, light 37 converges to the smallest portion of the beam. The resulting beam penetrates lens 52 and diverges following penetration of the lens. Specifically, light 37 diverges as is exits the lens (FIG. 6). This light illuminates a portion of retina 25 at the back of the patient's eye. Light 37 (FIG. 12) reflects off of the retina 25 into imaging portion 51 and then to imaging path 21, as shown in FIGS. 2 and 11.

Aperture 54 is positioned between patient's eye and imaging optics, as shown in FIGS. 2, 3 and 4. Aperture 54 blocks Purkinje reflections 55. More specifically, as light penetrates lens 52, some light is reflected off of, e.g., the back of the lens. These reflections are known as Purkinje reflections. Purkinje reflections can adversely impact retinal imaging by "fogging" or causing a "flare" in resulting images.

Surfaces 56 that form aperture 54 prevent at least part of the Purkinje reflections from reaching imaging path 21, thereby improving image quality. Surfaces 56 may be coated with a non-reflective material. This helps to reduce stray light in the system.

As shown in FIG. 2, some light 57 that is reflected from retina 25 may make its way through aperture 54 and into imaging path 21. There, light 57 passes through optics 59. Optics 59 include one or more lenses, which may be convex and/or concave. Optics 59 direct light 57 to aperture 60. Aperture 60 is used to "clean up" the edges of the image in the first focal plane. Its size is determined precisely by the optics between it and the eye. That is, light outside of aperture 60 is stray and can adversely affect imaging. Aperture 60 therefore is sized to allow light reflected from retina 25 to pass, while blocking some other light (e.g., reflections within imaging path 21). An identification mark, such as a tab, may be added to aperture 60, which would show-up on resulting images to thereby identify a patient, imaging parameters, or the like. Surfaces 61 that define aperture 60 may be coated with non-reflective material in order to reduce reflections in imaging path 21.

Imaging path 21 includes a second aperture 62 (FIG. 2). The size of aperture 62 can be adjusted. This aperture is at the "homogenized portion" of the imaging rays, not a focal plane. It behaves as an aperture stop in a standard camera which, when reduced in size or "stopped-down", removes peripheral rays, not peripheral image rays, which usually produce the worst aberrations of the image since they have come through lenses at the most extreme angles. These rays are emanated directionally from the retina (and thus are stereo). So blocking of left or right rays blocks those seen from a left or right perspective without blocking any portion of the image. Since the left or the right half of the rays are blocked, half the light (one f-stop) is lost in each of the images. Surfaces 64 that define aperture 62 may be coated with non-reflective material in order to reduce reflections in imaging path 21.

Figure 7:
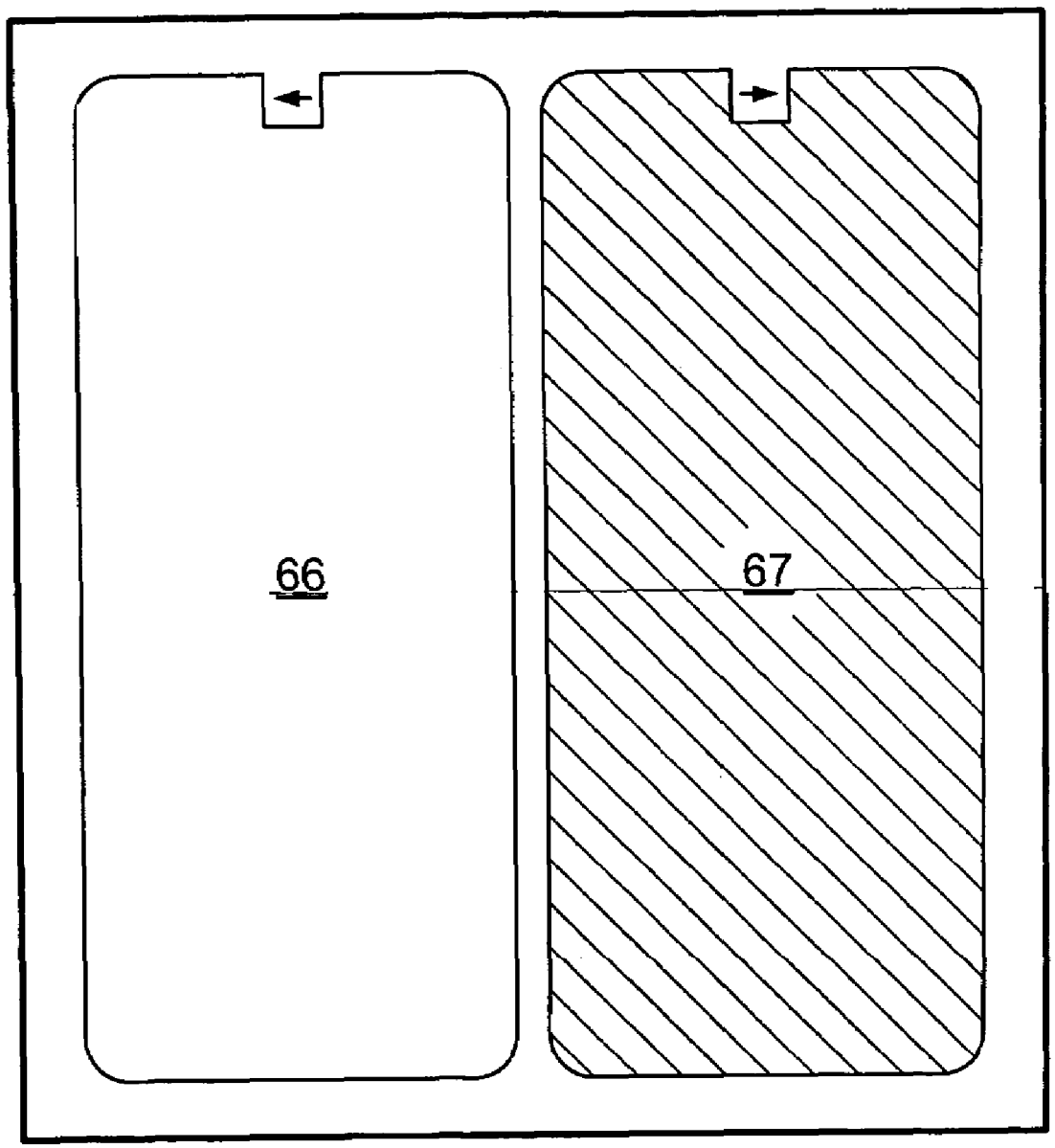
FIG. 7 is a front view of a stereo filter used in the retinal imaging system.

Light from aperture 62 passes to "stereo filter" 65. The "stereo filter" defines, e.g., a "shutter" that optionally blocks either the left or right half of the light rays. As shown in FIG. 7, stereo filter 65 contains an area 66 for transmitting/ blocking a first portion of imaging rays and another area 67 for transmitting/blocking a second portion of imaging rays. More specifically, areas 66 and 67 receive light from the same point on the patient's retina, however at different angles. By passing light in a first area, such as area 66, while blocking light in a second area, such as area 67, an image is obtained from one angle. By blocking light from the second area while allowing light to pass from the first area (without moving the system), it is possible to image the same area of the retina from a different angle. The general concept replicates depth perceived via two eyes.

In order to obtain true color with stereo image pairs, six exposures may be taken, comprising left and right versions of each of red, green, and blue. The stereo filter and the red, green and blue light sources (e.g., diodes) are synchronized with the frame rate of the camera in order to obtain the images. Currently this is 1/30 of a second, but this may be 1/60 of a second or better. A means of delivering the light to the illumination module and a "light switch" (described below) allow the colors to be sequenced red-green-blue. A left-right shutter mechanism within the imaging system allows the left-right (LR) stereo shutter to be synchronized with the red, green and blue (RGB) frames and all are sequenced with the camera frame rate. It is possible to capture numerous frames of each type, rather than just RL-RR-GL-GR-BL-BR, e.g., RL-RL-RL-RR-RR-RR-GL-GL-GL-GR-GR-GR-BL-BL-BL-BR-BR-BR, etc. (the first letter, e.g., "G" indicates color (green) and the second letter, e.g., "L" indications position (left)). Software can select the best "average" frame of each type, e.g., RL, GL, BL, RR, GR, BR, for processing to produce a color image.

The foregoing method allows the retinal imaging system to take a series of each type of image that is the duration of one heart beat. An "average" picture of each type would be selected for the same part of the heart beat as each of the others. This would result in averaging approximately 25 to 30 frames for each type of frame. Even with this large number of frames being taken, a complete exam of the Early Treatment Diabetic Retinopathy (ETDRS) protocol for seven stereo standard field dilated eye photography would take only 42 seconds for each eye.

Stereo filter 65 can be controlled manually or automatically to pass/block light from one area 66 or the other area 67. For example, stereo filter can be removed, inverted, and re-inserted into imaging path 21. Alternatively, stereo filter 65 may incorporate shutters or other similar devices to block light from one area or the other (e.g., left or right). Stereo filter may be removed (either automatically or manually) to enable imaging using the full amount of reflected light.

Optics 69, which may include concave and/or convex lenses, transmit light from stereo filter 65 to image capturing device 70 or to an observer. Image capturing device 70 may be a standard imaging camera such as a JAI-CV-A11 that captures retinal images from reflected light. For example, image capturing device 70 may be a camera, either digital or analog, that transmits data corresponding to retinal images to a computer, to film (e.g., 35 mm), or to an observer. For example, left and right images (obtained via the stereo filter) may be both presented to a screen and viewed with a special optical viewing device in a static display mode, or alternately presented on the same screen at 1/30 of a second in a dynamic display mode where LCD shuttered stereo viewing glasses such as Crystal Eyes manufactured by Stereographics synchronized to the screen display of the retinal images allows flicker free 3-dimensional viewing of the retinal images. One example of post-processing is combining images from areas 66 and 67 of stereo filter 65 to produce a simulated 3D image of the patient's retina. Another example of post-processing involves capturing and combining images using different color light. More specifically, as noted above, light source 27 may include red, green, blue, or other color diodes which emit red, green, blue light, or other color light. Illuminating the diodes separately, and obtaining images using colored light, has its advantages in that different colored light can accentuate different retinal features.

Thus, retinal imaging system 20 may be used to obtain six images of the same area of a patient's retina: a left red image, a right red image, a left green image, a right green image, a left blue image, and a right blue image, where "left" corresponds to an image from area 66 of stereo filter 65, and "right" corresponds to an image from area 67 of stereo filter 65. These images may be viewed separately or combined by use of one of the special viewers mentioned above to simulate an overall image having a 3D effect.

Figure 8:
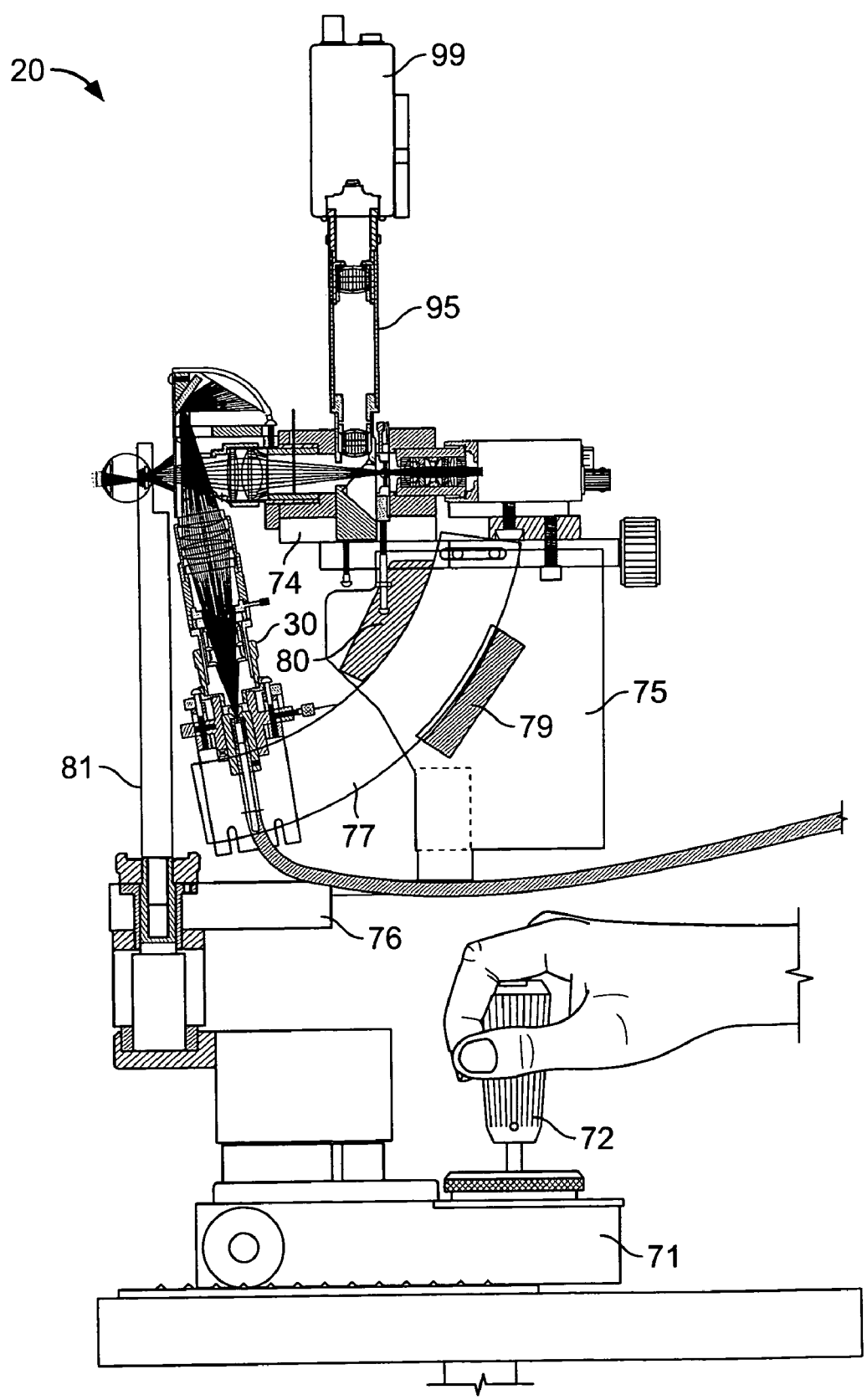
FIG. 8 is a side view of the retinal imaging system of FIG. 1 mounted to a slit lamp base.

Referring to FIG. 8, retinal imaging system 20 may be mounted on a slit lamp base 71 so that its motion can be controlled via a joystick 72 or similar device. Housing 74 (in which the structures that make up imaging path 21 reside) is mounted to base 71 via mounting plate 75 (or other component). Mounting plate 75 is connected to slit lamp base 71 via arm assembly 76 which can pivot about a vertical axis allowing lateral angle change to view parts of the retina off to the side. The joystick moves the entire assembly in-out, or left-right, or in some cases, up-down. In other cases, there is a separate wheel around the joystick that performs the up-down function.

Housing 30 (in which the structures that make up assembly 22 reside) is mounted to arc 77. Arc 77 is connected to mounting plate 75 via plates 79 and 80 or similar mechanism. Housing 30 is mounted such that it can be moved along arc 77 to view different areas of the patient's retina. Thus, retinal imaging system 20 provides five degrees of freedom of motion vis-à-vis a patient's eye (i.e., movement along standard Cartesian XYZ coordinates, as well as movement along altitude and azimuth directions). This allows for precision imaging of the patient's retina.

Figure 9:
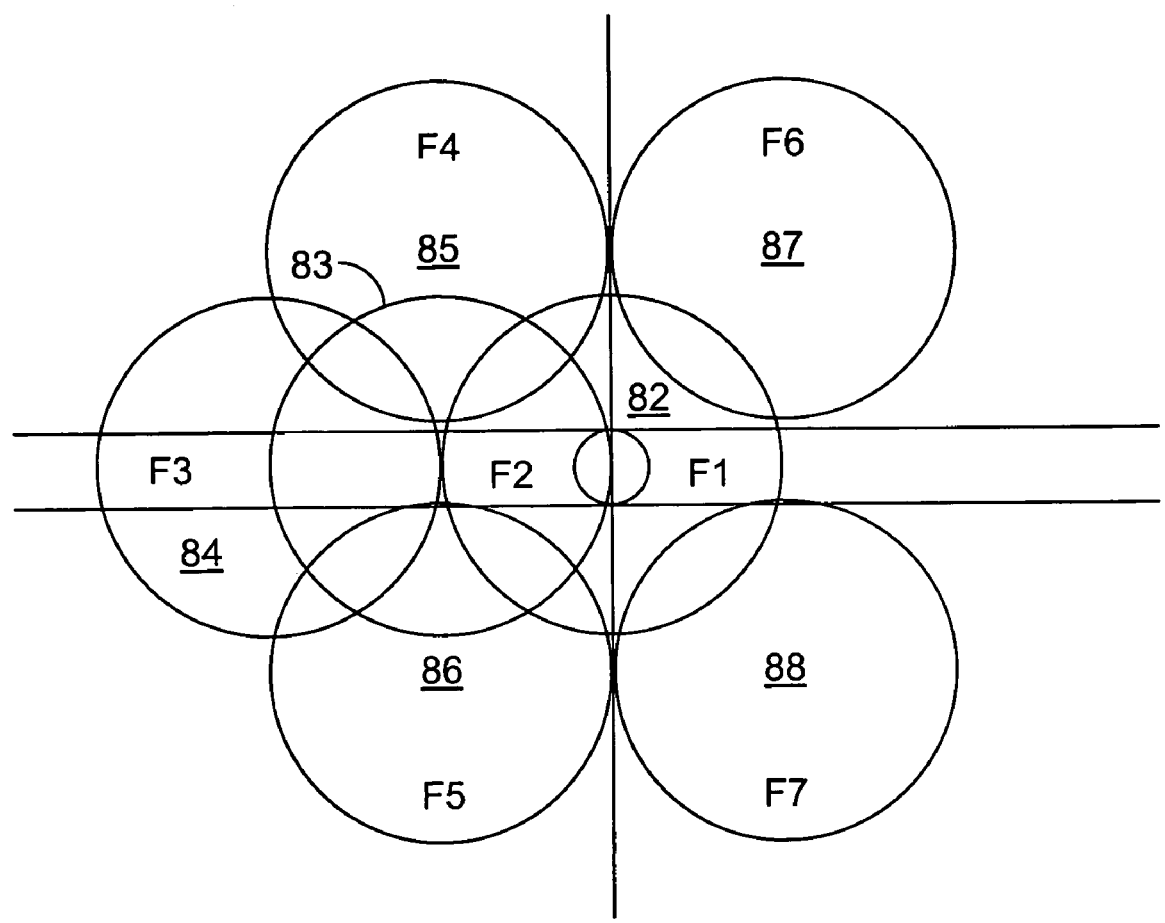
FIG. 9 is a diagram of the seven standard fields used in diabetic retinopathy.

In one embodiment, retinal imaging system 20 can thus be used to obtain images of the "ETDRS protocol seven standard fields" of the patient's retina. Referring to FIG. 9, the seven standard fields comprise seven 30° fields, which constitute the "gold standard" of diabetic retinopathy assessment. Field one (82) is centered on the optic disc; field two (83) is centered on the macula, and field three (84) is just temporal to the macula. Fields four (85), five (86), six (87), and seven (88) are tangential to horizontal lines passing through the upper and lower poles of the disc and to a vertical line passing through its center.

Figure 10:
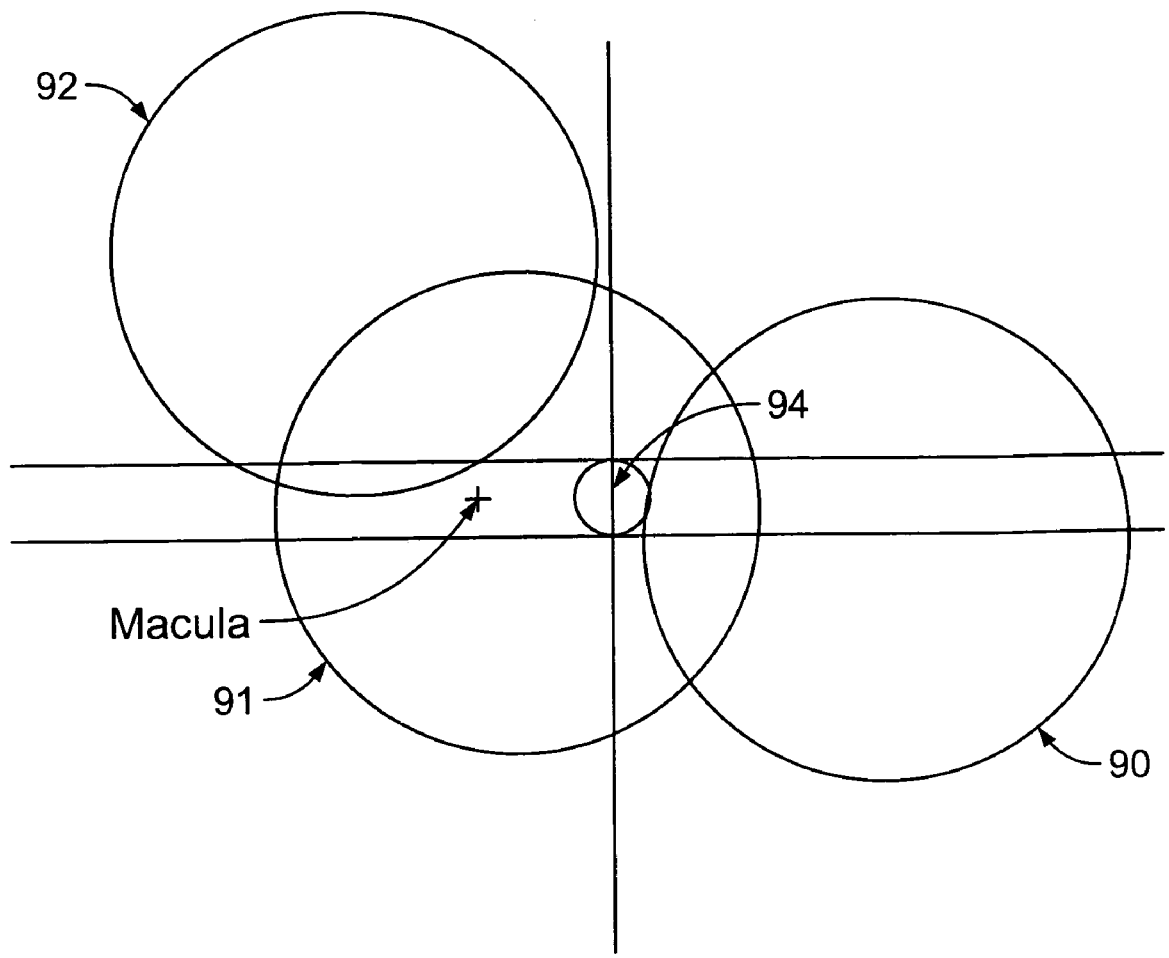
FIG. 10 is a diagram of three retinal fields that may be imaged using the retinal imaging system of FIG. 1.

In alternative embodiments, system 20 is movable so that images of the retina other than the "ETDRS protocol seven standard fields" can be captured. For example, as shown in FIG. 10, retinal imaging system 20 may be used to capture three fields 90, 91 and 92. These fields may be 35° to 37° fields, as opposed to the 30° fields noted above. Field 91 includes optic disc 94 and macula; field 90 is to the left of or nasal to the optic disc 94; and field 92 is to the right of field 91 or superior temporal to the optic.

Referring to FIG. 8, retinal imaging system 20 may also contain manual alignment system 95. Alignment system 95 includes a beam splitter 96 placed in imaging path 21. Beam splitter 96 directs a small portion of imaging light (as little as one or two percent) from imaging path 21, through lenses 97, to alignment camera 99. Alignment camera 99 captures a video macro-image of the illumination of a patient's eye and displays that image to a user. Based on this image, a user can move retinal imaging system 20 so that an appropriate area of the retina is illuminated. Alignment of retinal imaging system may be manual or automatic. Automatic alignment systems may incorporate computer, or other processor-based, controls.

Retinal imaging system 20 is nonmydriatic, meaning that eye drops are not required to pharmacologically dilate the pupil of the eye in order to obtain retinal images. A retinal imaging system may be used in any ophthalmic field, but has particular applicability to diabetic retinopathy and related disciplines.

Retinal imaging system 20 may be incorporated into an ophthalmoscope that performs functions in addition to those noted above. An ophthalmoscope is a lighted instrument used to examine the inside of the eye, including, but not limited to, the retina and the optic nerve.

In a second embodiment illustrated in FIG. 11, illumination path 100 and imaging path 101 are re-positioned. The second provides axial illumination (i.e., the illumination path is "on axis" with the patient's eye). Features of illumination path 100 and imaging path 101 that do not differ from the illumination path and imaging path of the first embodiment are not described.

The benefits of axial illumination are as follows. An axial illumination system allows the illumination to be rotated about the eye's optical axis. Since the illumination enters the eye off-center, and slightly tilted, rotating the illumination source creates a moving shadow which calls attention to any features of the retina that are raised or depressed, enhances any three-dimensional effect observed in stereo images, and avoids local opacities (e.g., cataracts) while maintaining full illumination. Furthermore, motion of the illumination system can be accomplished with only one moving part in an axial system. Traditional illumination may require rotation of the entire illumination. Still further, rotating the illumination system about its axis, while viewing real-time color stereo images, allows an observer to view any three-dimensional effects "in motion". This provides the observer with a better view of such effects.

In the first embodiment, the entire device may have to be rotated about angular axes of theta and phi in addition to the X,Y, and Z translational axes to view all but the central field (field 2 of the seven standard fields). In the second embodiment, viewing the image via a pellicle or beam splitter, rather than directly, we are enabled to "wobble" those reflectors about the imaging axis and sequence the seven standard fields.

In either embodiment, each diode may be coupled via optics (e.g., lenses, fibers, optical fluid, etc.) to an optical switch synchronized to an imaging CCD or other video imaging device. The optical switch, which may have an encoder built-in, positions the fiber that delivers the light to the illumination optics and ultimately to the retina, relative to the light from each color diode. This method of switching colors provides the freedom to obtain the programming sequences noted above. The encoder is in communication with the computer controlling the camera with which the diode aligned with, thereby enabling synchronization of the stereo filter. Another benefit of taking multiple frames of each type (red, green, blue, left, right—RGB, LR) is that the sequencing of the colors and stereo shutter can be virtually stopped for many frames, thus eliminating most vibration between those frames.

Figure 13:
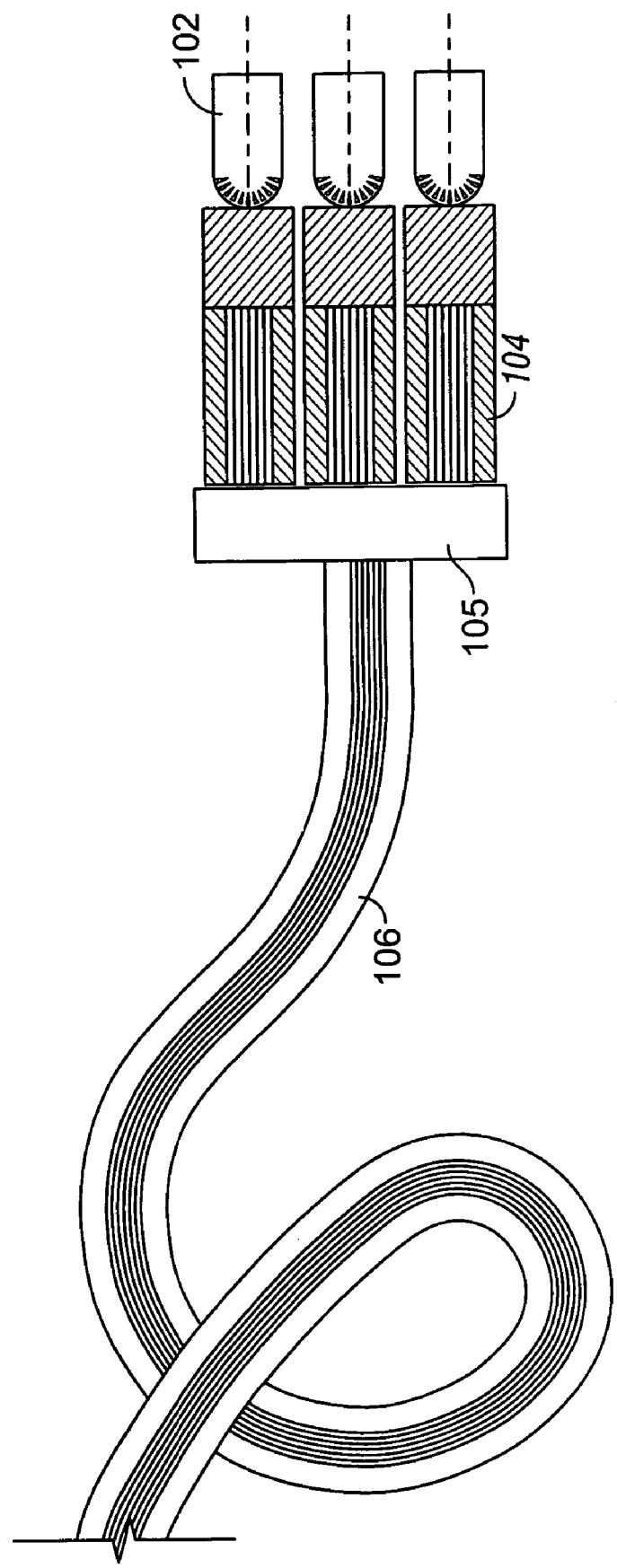
FIG. 13 is a side close-up view of diodes of an illumination system that may be used in either the first or second embodiment.

As shown in FIG. 13, each diode 102 may be coupled to a relatively short optical fiber 104 by the use of a lens, special refractive fluid, special anti reflective coatings, specially-shaped diode surface, or other means. The short fiber may be attached to an optical switch 105 which aligns the long fiber 106 transmitting the light to the illumination system with the short fiber. The long fiber has 2 functions: (1) it allows the diode assembly to be remote from the optical head of the imager to enable the optical head to be relatively small, and (2) it is flexible, so one end can be precisely positioned relative to each short fiber. The encoder in the optical switch informs the computer when to light each diode so that only the short fiber that is aligned with the long fiber receives light from its diode.

An additional change in the second embodiment is to place a thin, small angular prism 107 (FIG. 11) in front of the illumination system. This prism tilts rays from the illumination system to an angle that reduces reflections. The prism is rotatable about the illumination axis such that it can deliver illumination into the pupil from any angle about the axis to create moving shadows. The prism also allows the device to be adjusted so as to avoid illuminating local opacities or other problem areas of the eye, or at least to enter the eye at the "least bad" angle.

The invention is not limited to the specific embodiments described herein. For example, the sizes and numbers of apertures may vary in both the illumination and imaging paths. The specific optics used to direct and shape light in both the illumination and imaging paths may vary depending upon the character and quantity of light received from the light source, the shape of the eye being viewed, and the like (and working distance desired as well as many other factors). Light sources other than multi-colored diodes may be used. For example, one or more white diodes combined with optical color filters may be used in lieu of separate red, green and blue diodes. Media other than fiber optic cable may be used to deliver light from the light sources into the illumination path housing. A single integrated housing may be used to hold both the illumination path and the imaging path. Alternatively, separate housings may be used, as described.

Different configurations may be used for the beam absorption assembly. For example, mirror 41 may be omitted and light absorbing surface 42 may be repositioned in the location of mirror 41 but further away In this and the mirror system, the further away the components are the more spread the light is before hitting any surface. Similarly, more than one mirror may be used to direct light further away from imaging path 21 (e.g., around corners) to one or more light absorbing surfaces, which may be the same as, or different from, the light absorbing surface described above.

Alignment system 95 may be replaced with a computer-controlled automatic alignment system that does not rely on light siphoned from imaging path 21. Similarly, different types of manual alignment systems may be used.

Retinal imaging system may function without stereo filter 65. For example, stereo filter 65 may be removed and replaced with other optical or non-optical components.

Image capturing device 70 may be a film-based camera, a digital camera, or a video camera. Retinal imaging system may be mounted to surfaces or devices other than a slit lamp base.

To summarize, the retinal imaging system is a low light, nonmydriatic device enabling imaging through less than average pupil imaging diameters to 2.5 mm or even less that are characteristically experienced by subjects in low ambient light conditions. Monochromatic red, green and blue images are obtained and merged to produce a merged color image. Stereo images can be captured with consistent separation. The system relies on a point source illumination and, thus, has the potential to avoid imaging through local cataracts or other aberrant localized opaque optical structures in the eye.

The illumination path is largely separated from the imaging path within the eye, thus allowing imaging through diffuse cataracts. A high voltage flash illumination source has been eliminated in favor of solid state illumination. This allows for separate RGB images to be acquired and further reduces the lower sensitivity problem of color cameras. The retinal imaging system has sufficient efficiency to allow for live video (monochrome) without leaving substantial (or, in some cases, any) after-image. The retinal imaging system may be hand-held or table-mounted to provide ease of use under a variety of conditions. The retinal imaging system is designed to operate under low imaging light conditions thus ensuring patient comfort and safety.

In further embodiments, the retinal imaging system is able to capture live video in full color at ten frames per second or five fps in stereo, can align automatically to track a subject's eye, can separately adjust each color's exposure, and redirect the illumination to avoid local opacities and enhance three-dimensional eye features. Auto-alignment may be vis-à-vis the seven standard fields, resulting in an entire exam of one eye that takes about seven to ten seconds and delivers five sets of redundant frames (allowing software to select the best of each set of five frames).

Retinal imaging system 20 is useful in a variety of routine and specialized eye examinations, and is useful to detect or diagnose eye diseases or conditions in patients, and is particularly useful to diagnose patients with characteristically small pupils and/or whose pupils do not dilate significantly under low ambient light conditions. Increasing age and diabetes are two conditions that prevent (or at least inhibit) adequate pupil dilation under low ambient light conditions. In this regard, the greater proportion (80%) of patients with diabetes have type 2 diabetes, which means that they are generally older. In addition, patients over age 60 without diabetes will characteristically have smaller pupils. With an aging population, there is an increasing risk for diabetes and Age Related Macular Degeneration (AMD). AMD is one of the conditions that can be identified using the retinal imaging system. Also, as diabetic patients now tend to live longer, they will have increasing years of disease duration. Thus, the longer patients have diabetes, the more likely it is that they will have smaller pupils.

Another medical condition which results in patients having relatively small pupils is following treatment for glaucoma. The retinal imaging system can be used to monitor progression of glaucoma in the retina. Also, diabetic patients will suffer from glaucoma and will need to be treated. Other examples of medical conditions which result in patients having relatively small pupils include various neurological conditions, such as Horner's syndrome and neurological syphilis.

The retinal imaging system may also be used in diagnostic procedures to identify and assess a number of ocular pathologies not related to diabetes. These include, but are not limited to, cataract, Optic Cup/Disc asymmetry as a risk for glaucoma, macular drusen and retinal pigment epithelial changes as a risk for age related macular degeneration, age related macular degeneration, hypertensive retinopathy, retinal emboli as a risk for cardiovascular disease, retinal vein occlusion, preretinal hemorrhage, vitreous hemorrhage, traction retinal detachment, choroidal nevus and choroidal lesions, epiretinal membrane, asteroid hyalosis, chorioretinal scar/atrophy, optic disc hemorrhage, and macular hole.

The retinal imaging system may be used to diagnose both mammalian and non-mammalian subjects, and invertebrates and non-invertebrate subjects. The retinal imaging system may be used with living or dead subjects and with ocular models.

Elements of the first and second embodiments may be combined to produce a different embodiment not specifically described herein.

Other embodiments not described herein are also within the scope of the following claims.

What is claimed is:

1. A retinal imaging system comprising:
    a light source;
    optics configured to receive light from the light source and to transmit the light so that the light converges prior to entering an eye along a first axis, forms a beam that passes through a lens of the eye, remains substantially collimated through the lens, and diverges upon exiting the lens to illuminate an area of a retina of the eye; and
    an imaging device to receive imaging rays produced by a reflection of the light from the retina, wherein the imaging rays exit the eye along a second axis that is separate and different from the first axis.

2. The retinal imaging system of claim 1, wherein the optics comprise a beam splitting device that allows transmission of at feast part of the light away from the eye.

3. The retinal imaging system of claim 2, further comprising:
    a darkened region for absorbing the part of the light transmitted away from the eye.

4. The retinal imaging system of claim 1, further comprising:
    a surface containing an aperture that is positioned in front of the eye for blocking at least some Purkinje reflections and corneal reflections from the eye.

5. The retinal imaging system of claim 4, wherein the surface is covered, at least in part, with a non-reflective material.

6. The retinal imaging system of claim 1, further comprising:
    surfaces that form an aperture located between the light source and the optics, the aperture limiting an angle of the light to reach the optics.

7. The retinal imaging system of claim 1, further comprising a series of surfaces that form a series of apertures located between the light source and the optics, the series of apertures limiting an angle of the light to reach the optics.

8. The retinal imaging system of claim 1, further comprising rilling located along a path the light takes between the light source and the optics.

9. The retinal imaging system of claim 1, further comprising a stereo filter located on an optical path between the eye and the imaging device, the stereo filter comprising an area for transmitting a first portion of the imaging rays from the eye and an area for blocking a second portion of the imaging rays.

10. The retinal imaging system of claim 9, wherein the first portion of the imaging rays comprise rays obtained at a first angle from a point on the retina, and the second portion of the imaging rays comprise rays obtained at a second angle from the point on the retina.

11. The retinal imaging system of claim 1, further comprising:
    at least one housing that holds the light source, the optics, and the imaging device; and
    a mechanism for positioning the at least one housing relative to the eye.

12. The retinal imaging system of claim 1, further comprising:
a housing that holds at least part of the optics, the housing being movable to change the area of the retina that is illuminated.

13. The retinal imaging system of claim 1, wherein the light source comprises:
light emitting diodes having different colors; and optical fiber arranged to receive light from at least one of the light emitting diodes.

14. An ophthalmoscope comprising:
optics configured to direct light into a predetermined portion of an eye that is not used for imaging, the light entering the eye along a first axis, the optics for shaping the light so that the light converges prior to entering the eye, forms a beam that passes through a lens of the eye, remains substantially collimated through the lens, and diverges upon exiting the lens to illuminate an area of a retina of the eye; and
an imaging device to capture images of the retina from imaging rays produced by a reflection of the light from the retina, wherein the imaging rays exit the eye along a second axis that is separate and different from the first axis.

15. The ophthalmoscope of claim 14, wherein the optics comprise
a beam splitting device that transmits at least part of the light away from the eye.

16. The ophthalmoscope of claim 15, further comprising:
a darkened region for absorbing the part of the light transmitted away from the eye.

17. The ophthalmoscope of claim 14, further comprising:
a surface containing an aperture that is positioned in front of the eye for blocking at least some Purkinje reflections from the eye.

18. The ophthalmoscope of claim 17, wherein the surface is covered, at least in part, with a non-reflective material.

19. The ophthalmoscope of claim 14, further comprising:
a light source that provides the light to the optics; and
surfaces that form an aperture located between the light source and the optics, the aperture limiting an angle of the light to reach the optics.

20. The ophthalmoscope of claim 14, further comprising a series of surfaces that form a series of apertures located between the optics and a source of the light, the series of apertures limiting an angle of the light to reach the optics.

21. The ophthalmoscope of claim 14, further comprising rilling located along a path the light takes between a source of the light and the optics.

22. The ophthalmoscope of claim 14, further comprising a stereo filter located on an optical path between the eye and the imaging device, the stereo filter comprising an area for transmitting a first portion of the imaging rays from the eye and an area for blocking a second portion of the imaging rays.

23. The ophthalmoscope of claim 22, wherein the first portion of the imaging rays comprise rays obtained at a first angle from a point on the retina, and the second portion of the imaging rays comprise rays obtained at a second angle from the point on the retina.

24. The ophthalmoscope of claim 14, further comprising:
a light source that provides the light to the optics;
at least one housing that holds the light source, the optics, and the imaging device; and
a mechanism for positioning the at least one housing relative to the eye.

25. The ophthalmoscope of claim 14, further comprising:
a housing that holds at least part of the optics, the housing being movable to change the area of the retina that is illuminated.

26. The ophthalmoscope of claim 14, further comprising a light source, the light source comprising:
light emitting diodes having different colors; and
optical fiber arranged to receive light from at least one of the light emitting diodes and to deliver the light to the optics.

27. A retinal imaging apparatus, comprising:
means for producing convergent light and for directing the convergent light to a lens of an eye to form a beam that passes through the lens, remains substantially collimated in the lens, and diverges after exiting the lens to illuminate an area of a retina of the eye, the convergent light entering the eye along a first axis;
means for capturing an image of the retina from imaging rays produced by a reflection of light from the retina, wherein the imaging rays exit the eye along a second axis that is separate and different from the first axis;
means for selectively blocking light reflected from a cornea of the eye; and
means for capturing light reflected from the retina.

28. A retinal imaging system comprising:
an illumination path system configured to receive light and to cause the light to penetrate a pupil of an eye at a spot on the pupil, the light entering the eye along a first axis and exiting a lens of the eye along a second axis that is separate and different from the first axis to illuminate an area of a retina of the eye, wherein the illumination path system is configured to cause the light to converge toward the lens, to substantially collimate in the lens, and to diverge upon exiting the lens; and
an imaging path system confirmed to receive reflected light from the area of the retina and to transmit the reflected light to an imaging device, the imaging path system containing surfaces that define apertures to reduce Purkinje reflections and to reduce reflections from an iris of the eye, the imaging path system containing a stereo filter having one area for passing a first portion of the reflected light and another area for blocking a second portion of the reflected light.

29. The retinal imaging system of claim 28, further comprising:
a base on which the illumination path system and the imaging path system are mounted, the base providing five degrees of freedom of motion for the retinal imaging system.

30. The retinal imaging system of claim 29, wherein the base comprises a slit lamp base.

31. The retinal imaging system of claim 28, wherein the illumination path system comprises a beam splitting device that transmits at least part of the light away from the eye.

32. The retinal imaging system of claim 31, further comprising:
a darkened region for absorbing the part of the light transmitted away from the eye.

33. The retinal imaging system of claim 28, wherein the illumination path system comprises a series of surfaces that form a series of apertures located along the illumination path system, the series of apertures limiting an angle of the light to reach the eye.

34. The retinal imaging system of claim 28, further comprising rilling located along the illumination path system.

35. The retinal imaging system of claim 28, wherein the first portion of reflected light comprises light reflected at a first angle from a point on the retina, and the second portion of reflected light comprises light reflected at a second angle from the point on the retina.

36. The retinal imaging system of claim 28, further comprising:
a light source comprised of different color diodes which provide the light to the illumination path system.

37. The retinal imaging system of claim 28, further comprising:
a beam splitter that transmits at least part of light from the illumination path system away from the eye.

38. A method comprising:
generating convergent light via an illumination path system of a retinal imaging system;
directing the convergent light through an illumination portion of an eye such that the light enters the eye along a first axis, converges towards a lens of the eye, remains substantially collimated through the lens, and diverges after exiting the lens, the illumination portion of the eye being segregated from an imaging portion of the eye;
receiving reflected light via the imaging portion of the eye;
passing the reflected light through an imaging path system to an image capturing device;
positioning the imaging path system relative to the illumination path system such that the reflected light exits the eye along a second axis that is separate and different from the first axis; and
producing an image based on the reflected light.

39. The method of claim 38, further comprising:
selectively blocking a portion of the reflected light to produce a stereo image of the eye.

40. The method of claim 39, wherein selectively blocking comprises transmitting a first portion of the reflected light and blocking a second portion of the reflected light.

41. The method of claim 40, wherein the first portion comprises rays obtained at a first angle from a point on the retina, and the second portion comprises rays obtained at a second angle from the point on the retina.

42. The method of claim 38, further comprising:
blocking at least some Purkinje reflections from reaching the imaging path.

43. The method of claim 38, wherein the convergent light is generated via one or more of optics, rilling, apertures, and colored diodes.

44. A method of diagnosing a condition comprising:
directing light along an illumination path system which receives light, and causes the light to enter a pupil of an eye along a first axis, the illumination path system causing the light to converge towards a lens of the eye, to substantially collimate through the lens, and to diverge after exiting the lens;
passing reflected light produced by a reflection of the light from a retina of the eye through an imaging path system which transmits the reflected light to an imaging device;
positioning the imaging path system relative to the illumination path system such that the reflected light exits the eye along a second axis that is separate and different from the first axis; and
generating images via the imaging device that include shadows indicative of details of the eye.

45. The method of claim 44, wherein generating images comprises generating video images.

46. A retinal imaging system comprising:
a light source:
optics configured to receive light from the light source and to transmit the light so that the light is substantially convergent, the light entering an eye along a first axis, penetrating a lens of the eye, and diverging following penetration of the lens to illuminate an area of a retina of the eye, the light converging until reaching the lens; and
an imaging device to receive imaging rays produced by a reflection of the light from the retina, wherein the imaging rays exit the eye along a second axis that is separate and different from the first axis;
wherein the optics are configured to direct the light from the light source to the eye along an illumination path system; and
a mechanism for rotating the illumination path system relative to the eye.

47. The retinal imaging system of claim 46, wherein the beam substantially collimates through the lens and diverges upon exiting the lens to illuminate the area of the retina.

* * * * *